United States Patent [19]

Nakamura

[11] Patent Number: 5,776,464
[45] Date of Patent: Jul. 7, 1998

[54] AGENT FOR RELIEVING SIDE EFFECTS CAUSED BY IMMUNOSUPPRESSANTS

[76] Inventor: Toshikazu Nakamura, 10-27, Takamidai, Takatsuki-shi, Osaka 569, Japan

[21] Appl. No.: 716,141

[22] PCT Filed: Mar. 1, 1995

[86] PCT No.: PCT/JP95/00329

§ 371 Date: Nov. 13, 1996

§ 102(e) Date: Nov. 13, 1996

[87] PCT Pub. No.: WO95/25537

PCT Pub. Date: Sep. 28, 1995

[30] Foreign Application Priority Data

Mar. 18, 1994 [JP] Japan ................................. 6-074272

[51] Int. Cl.[6] ........................... A61K 39/00; A61K 38/18
[52] U.S. Cl. .......................... 424/198.1; 514/12; 514/21
[58] Field of Search ..................... 424/198.1; 514/12, 514/21

[56] References Cited

PUBLICATIONS

Takada et al., Transplantation Proceedings, vol. 28, No. 2, 1089–1090 (Apr. 1996).
Amaike et al., Cytokine, vol. 8, No. 5, 387–394 (May 1996).
Physicians' Desk reference, 48th Edition (1994).
Strain et al. J. Clin. Invest. 1991 (May), 87(5): 1853–7.
Matsumoto et al. Bioch Bioply Res Comm 1992 vol. 188 pp. 235–243.
Li et al In Vitro Cellular & Developmental Biol. May 1992, vol. 28A:364–8.
Weidmer et al Proc. Natl Acad Sci 1991 Aug. 15 vol. 88: 7001–5.
Shiota et al Proc. Natl Acad Sci. 1992 Jan. 1 89:373–7.
Bussolino et al Joy Cell Biol 1992 Nov. 119:629–41.

*Primary Examiner*—Lila Feisee
*Assistant Examiner*—Geetha P. Bansal
*Attorney, Agent, or Firm*—Birch, Stewart, Kolasch & Birch, LLP

[57] ABSTRACT

The present invention relates to an agent for relieving side effects caused by immunosuppressants, which comprises HGF (Hepatocyte growth factor) as an active component, a method for relieving side effects caused by immunosuppressants, which comprises administration of HGF and use of HGF for producing an agent for relieving the side effects. HGF as an active component can reduce multiple-organ or systemic side effects caused by immunosuppressants. Therefore, according to the present invention, restrictions of use and dose of immunosuppressants are reduced, success rate of organ transplantation and cure rate of various patients to which the immunosuppressants are administered can be improved and at the same time burden of the patients can be remarkably reduced.

6 Claims, 1 Drawing Sheet

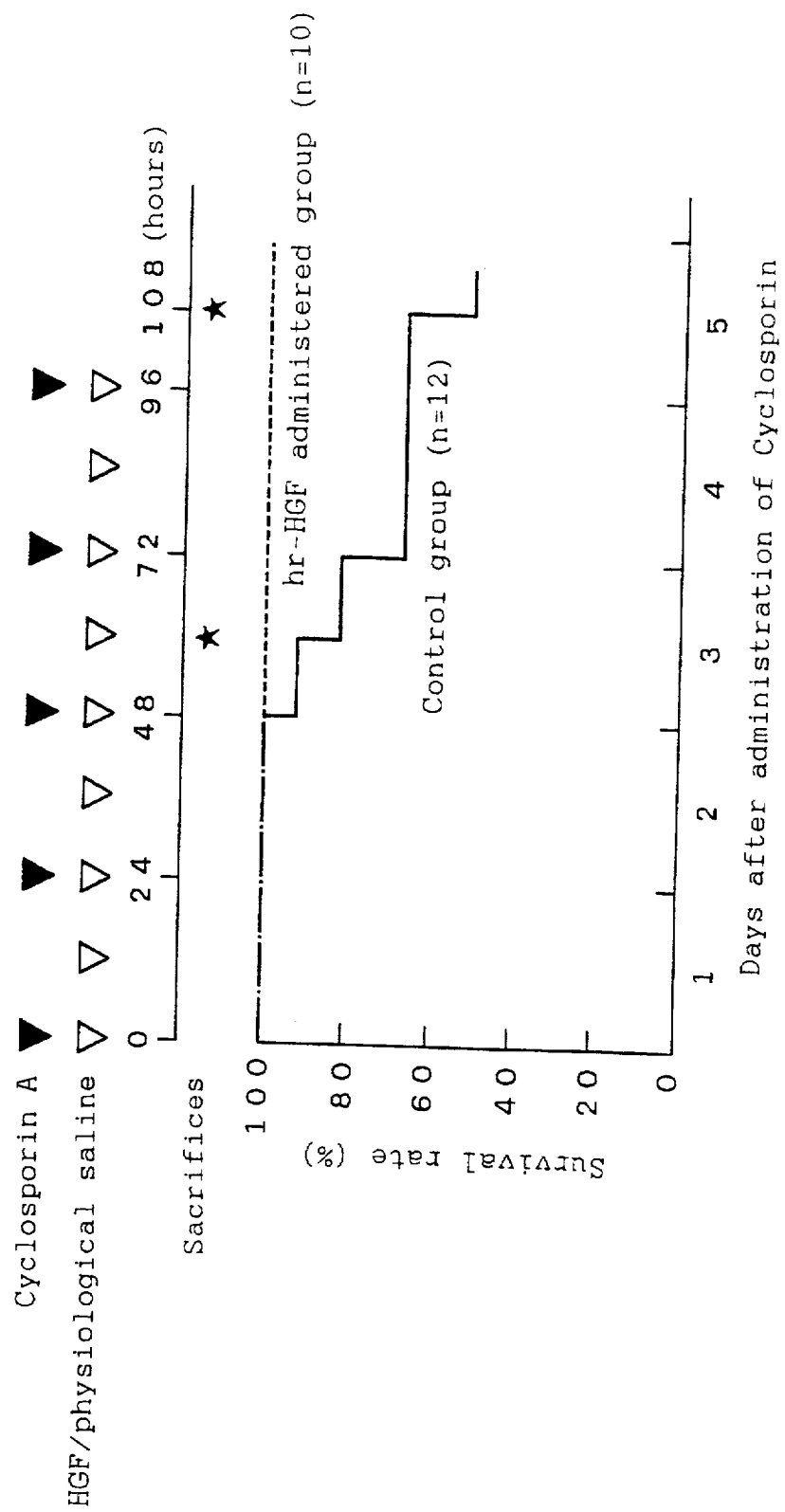

AGENT FOR RELIEVING SIDE EFFECTS CAUSED BY IMMUNOSUPPRESSANTS

TECHNICAL FIELD

The present invention relates to an agent for relieving side effects caused by immunosuppressants. More particularly, the present invention relates to an agent for relieving side effects which can ease side effects caused by immunosuppressants and which contains HGF (Hepatocyte Growth Factor) as an effective component.

BACKGROUND ART

An immunosuppressant is conventionally used for treatment of an autoimmune disease and malignant tumor, suppression of graft rejection reaction in organ transplantation and the like. An immunosuppressant is a medicine which suppresses an excessively occurring immune response, and is largely classified into a non-specific immunosuppressant or a specific immunosuppressant depending on its specificity of immunosuppression.

Examples of the non-specific immunosuppressant include an adrenocortical hormone (for example, cortisone, dexamethasone or the like), antimetabolic (for example, 6-mercaptopurine, azathiopurine, 5-fluorouracil, methotrexate or the like), alkylating agent (for example, cyclophosphamide, busulfan or the like), alkaloid (for example, vinblastine, vincristine or the like), antibiotic (for example, cyclosporin A and G, FK506 (tacrolimus), mitomycin C, daunorubicin or the like), and the like. Examples of the specific immunosuppressant include an anti-lymphocyte globulin, monoclonal antibodies (for example, anti-CD3 antibody, anti-CD4 antibody and the like) against various antigens expressed on the surface of a lymphocyte, and the like.

Among the above-described immunosuppressants, cyclosporin and FK506 have strong immunosuppression action and accomplish excellent results in suppression of graft rejection reaction in organ transplantation of a kidney, liver, heart, pancreas and the like, therefore, are noted medicine. Both of cyclosporin and FK506 are antibiotic immunosuppressants having a cyclic peptide structure, and is believed to express immunosuppressant effect by blocking an intracellular signal transfer path which introduces expression of a cytokine gene such as IL-2 or the like via activation of a T-cell antigen receptor (TCR) due to antigen stimulation in a T-cell system. More specifically, each one of cyclosporin and FK506 is known to be bound in a cell to a binding protein thereof, and cyclosporin is bound to cyclophilin and FK506 is bound to an FK506 binding protein. These binding proteins are called immunophilin, including their families. The following study revealed that a complex of immunophilin with FK506 or cyclosporin is bound to a serine/threonine dephosphorylation enzyme, calcineurin, and inhibits its enzymatic activity. And now, cyclosporin and FK506 are believed to express immunosuppressant action since a complex of immunophilin with them inhibits enzymatic activity of calcineurin. This theory is supported by the fact that there is a correlation between strength of inhibition of enzymatic activity of calcineurin by a derivative of cyclosporin and FK506 and strength of inhibition of IL-2 synthesis in their T-cells, or the like.

As described above, a lot of immunosuppressants are used, however, any medicine has side effects. For example, multiple-organ or systemic side effects have been reported, such as bone marrow suppression, leukopenia, thrombocytopenia, severe infectious disease, hepatic disorder, kidney disorder, neuropathy, lung disorder, gastrointestinal disorder, anorexia, nausea, vomiting, diarrhea, anemia, gingivostomatitis, alopecia, piloerection, chromatosis, hypotension, arrhythmia, fever, convulsion, infecundity, azoospermia, malaise and the like. Thus, immunosuppressants now used have problems that side effect is strong, dose thereof is restricted and careful attention is necessary in use.

More particularly, an immunosuppressant having strong bone marrow suppression causes leukopenia and easily manifests severe infectious disease, therefore, the dose thereof is necessary to be restricted. Then, acute rejection reaction easily to be manifested in organ transplantation, and dysfunction of transplanted organs often occurs. Cyclosporin and FK506 generally used in organ transplantation are medicines which suppress IL-2 synthesis by acting T-cells since they can remarkably reduce critical rate of acute rejection reaction after organ transplantation. Therefore, cyclosporin and FK506 have advantages that manifesting rate of bone marrow suppression is low, manifestation of severe infectious disease following leukopenia can be protected, and management after organ transplantation will be easier. Also due to these effects, the result of organ transplantation can be remarkably improved.

Further, even for cyclosporin and FK506, side effects are observed. For example, for cyclosporin, multiple-organ or systemic side effects such as nephrotoxicity, hepatoxicity, neuropathy, hypertension, caput femoris necrosis, cataract, diabetes, acute pancreatitis, cytomegalovirus infectious disease and the like have been reported, and the dose thereof is restricted. Especially in renal transplantation, kidney disorder based on nephrotoxicity has serious influence on aftercare of the transplanted kidney, and further in early period after the transplantation, the kidney disorder based on nephrotoxicity is difficult to be distinguished from renal insufficiency due to acute rejection reaction after the transplantation. Therefore, it is indispensable to monitor constantly cyclosporin concentration in blood and carefully control the dose, and if side effects by cyclosporin are recognized, the dose of cyclosporin should be reduced or the administration should be stopped, and after transplantation management against side effects is necessary. Further, the dose of FK506 can be reduced since FK506 is 100 times as active as cyclosporin, therefore side effects caused by FK506 can be reduced as compared with cyclosporin. However, as the side effects caused by FK506, multiple-organ or systemic side effects, for example, kidney disorder, anorexia, vomiting, pancreatitis, hyperkalemia, hyperuricemia and the like have been reported.

It is also reported that calcium-channel blocker and prostaglandin are useful in prevention of nephrotoxicity caused by cyclosporin (Transplantation 51, 293-295, 1991; Clin. Nephrol 25 [suppl. 1], S89-S94, 1986). However, these medicines have insufficient effect and can not suppress multiple-organ or systemic side effects.

As described above, immunosuppressants now used have severe multiple-organ or systemic side effects, therefore, there are many restrictions with respect to use and dose and a medicine is intensely required which can remarkably reduce the multiple-organ or systemic side effects of the immunosuppressants.

The present inventor has studied intensely on medicine which can reduce the side effects of the immunosuppressants to resolve the above-mentioned problems. As the result, the inventor has found that HGF can remarkably reduce the multiple-organ or systemic side effects of the immunosuppressants.

More specifically, HGF is a protein that the present inventor et al. have found as a factor which enhances proliferation of mature liver parenchyma cells in vitro and purified from serum of rats with regenerating liver (Biochem Biophys Res Commun, 122, 1450, 1984). Further, the inventor et al. have succeeded in isolation of HGF from rat blood platelets (Proc. Natl. Acad. Sci. 83, 6489, 1986; FEBS Letters, 22, 311, 1987), and have determined partial amino acid sequence thereof. Further, the present inventor et al. have succeeded in obtaining HGF as a protein by cloning HGF cDNA of human and rat origin utilizing the solved HGF amino acid sequence, and introducing the cDNA into animal cells by recombinant technique (human HGF: Nature, 342, 440, 1989; rat HGF: Proc. Natl. Acad. Sci. 87, 3200, 1990).

This HGF found as a factor which specifically proliferates liver parenchyma cells has been proved, by recent studies of a lot of researchers including the present inventor, to manifest various physiological activities in vivo and to be acting on therapy of injury of various organs and tissues. HGF is expected to be not only a research object but also a medicine applied to human or animal therapeutic agents.

In view of such action of HGF, the present inventor has thought that HGF must be useful for reduction of side effects caused by immunosuppressants and has studied the effect of HGF against side effects of immunosuppressants. As the result, it has been found that HGF can remarkably reduce multiple-organ or systemic side effects caused by immunosuppressants. It is a novel knowledge and an action of HGF which has conventionally not been known that HGF is effective in reduction of side effects caused by immunosuppressants.

The present invention has been accomplished based on such knowledge, and an object of the present invention is to provide an agent for relieving side effects caused by immunosuppressants.

DISCLOSURE OF THE INVENTION

The present invention is an agent for relieving side effects caused by immunosuppressants, which comprises HGF as an active component.

Other inventions of the present invention are a method for relieving side effects caused by immunosuppressants, which comprises administration of an effective amount of HGF and use of HGF for producing an agent for relieving side effects caused by immunosuppressants.

The above-mentioned HGF may be one derived from human or animal tissue or blood, or may be one produced by gene engineering.

Because cells on which HGF as an effective component acts exist in extremely wide range of organs and tissues, multiple-organ or systemic side effects caused by immunosuppressants can be reduced.

BRIEF DESCRIPTION OF THE DRAWING

FIG. 1 is a graph which shows experiment design and survival rate of mice.

BEST MODES OF CARRYING OUT THE INVENTION

As to HGF which is the active ingredient of the invention, any HGF can be used in the invention as long as it is purified to be able to use for a medicine, regardless of preparation methods of HGF. Many methods are known to prepare HGF, and, for example, HGF can be obtained by extraction and purification from organs such as liver, spleen, lung, bone marrow, brain, kidney, placenta and the like, blood cells such as platelets, leukocytes and the like, plasma and serum of mammals such as rat, cow, horse, sheep and the like. Also, it is possible to obtain HGF by cultivation of primary culture cells or cell lines producing HGF, followed by separation and purification from the culture product (e.g. culture supernatant, cultured cell, etc.). Further, HGF can be obtained by gene engineering method which comprises cloning the gene coding HGF with a proper vector, inserting it into a proper host cell to give a transformant, and separating the desired recombinant HGF from the culture supernatant of the transformant (e.g. Nature, 342, 440, 1989, Japanese Patent Kokai No. 111383/1993, Biochem. Biophys. Res. Commun., 163, 967, 1989). The host cell is not specifically limited, and various host cells conventionally used in gene engineering methods can be used, which are, for example, *Escherichia coli*, *Bacillus subtilis*, yeast, filamentous fungi, and plant or animal cells.

More specifically, the method of extracting and purifying HGF from live tissues is, for example, to administer carbon tetrachloride to a rat intraperitoneally, remove a liver from the rat with hepatitis, grind it, and purify by the ordinary protein purifying technique such as gel column chromatography using S-Sepharose and heparin Sepharose, HPLC and the like. Further, by the gene engineering method, the gene coding the amino acid sequence of human HGF is cloned into a vector such as bovine papilloma virus DNA and the like to obtain an expression vector, and by using this expression vector, animals cells such as Chinese hamster ovary (CHO) cells, mouse C127 cells, monkey COS cells and the like are transformed, and HGF can be obtained from the culture supernatant of the transformants.

As to HGF thus obtained, there are possibilities that a part of the amino acid sequence will be deleted or substituted with other amino acid(s), that another amino acid sequence is partially inserted, that 1, 2 or more amino acids are attached to the C and/or N terminals, or that sugars are similarly deleted or substituted. Such HGF analogues are disclosed in Japanese Patent Kokai No. 130091/1992 and PCT International Publication No. WO90/10651, and they may be also used in the invention and are included within the scope of the invention.

The above-described HGF can reduce multiple-organ or systemic various side effects caused by immunosuppressants as shown in Examples mentioned later. More specifically, nephrotoxicity, hepatoxicity, gastrointestinal disorder (for example, anorexia, diarrhea or the like), neuropathy (for example, weakness condition, irritation, convulsion or the like) and injury of organs are prevented, and recovery of organs is promoted, further, death rate due to side effects can be reduced.

Cells on which HGF acts exist in extremely wide range of organs and tissues such as, for example, liver cell, renal tubular epithelial cell, areolus epithelium, tunica mucosa ventriculi epithelium, blood vessel endothelium, cutis keratinocyte and the like. Therefore, HGF can effectively reduce multiple-organ or systemic various side effects caused by immunosuppressants.

A further important point in considering the practical use of HGF as medicine is that little side effect is recognized if HGF is administered to animals for long period. It is also a good feature that HGF promotes the growth of cells only in phase G1, that is, the cells only in the growth period, not cells in phase G0, that is, stationary period. It means that it promotes growth and regeneration of injured tissues, but does not act at all on intact tissues. Therefore, if HGF is administered excessively, or if HGF reaches non-ailing sites through blood or the like, it does not induce carcinogenic action or excessive growth in normal tissues.

The agent for relieving side effects of the present invention is applied for relieving side effects caused by the above-mentioned non-specific immunosuppressant or specific immunosuppressant in mammals (for example, cow, horse, pig, sheep, dog, cat and the like) including human, and manifests remarkable effect in reduction of side effects especially caused by antibiotic immunosuppressants such cyclosporin, FK506, mitomycin C, daunorubicin and the like. As described above, since action of HGF reaches wide range of organs and tissues, multiple-organ or systemic relieving of side effects beyond topical relieving of side effects can be accomplished.

The agent for relieving side effects in the invention may be prepared in various preparation forms (for example, liquid, tablet, capsule), and generally it is prepared in the form of injection containing HGF as the active ingredient alone or together with common carrier, or in the form of oral preparation together with common carrier. The injection may be prepared by the conventional method, and for example, HGF is dissolved in a proper solvent (for example, sterilized water, buffer solution, physiological saline), filtered and sterilized, and put in a container aseptically. The content of HGF in the injection may be usually 0.0002 to 0.2 w/v%, preferably 0.001 to 0.1 w/v%. As oral preparation, it is manufactured in various preparation forms, including tablet, granule, fine granule, powder, soft or hard capsule, liquid, emulsion, suspension or syrup, and these preparations may be manufactured by the conventional method. The HGF content in the preparation may be properly adjusted depending on the preparation form and the disease to be treated.

In production of the preparation, it is preferable to add a stabilizer, and examples of the stabilizer include albumin, globulin, gelatin, mannitol, glucose, dextran, ethylene glycol and the like. Moreover, the preparation of the invention may contain other additives necessary for pharmaceutical preparation, such as an excipient, a dissolving aid, an antioxidant, a pain-alleviating agent, an agent for isotonicity and the like. In liquid preparation, it is preferable to store it under frozen conditions or after the removal of water by a process such as freeze-drying. The freeze-dried preparation is used by dissolving again in distilled water for injection and the like before use.

The agent for relieving side effects in the invention is administered through various routes depending on the preparation form. For example, the injection is administered by intravenous, intraarterial, subcutaneous, intramuscular and the like. The dose is adjusted properly depending on symptoms, age and body weight of patient, and generally 0.01 mg to 100 mg of HGF is administered once or several times per day.

Industrial Applicability

In the present invention, HGF as the effective component can remarkably reduce side effects caused by immunosuppressants. Especially, since action of HGF reaches wide range of organs and tissues, multiple-organ or systemic relieving of side effects beyond topical relieving of side effects can be accomplished. Therefore, according to the present invention, restrictions of use and dose of immunosuppressants due to side effects are reduced, success rate of organ transplantation and cure rate of various patients to which the immunosuppressants are administered can be improved and at the same time burden of the patients can be remarkably reduced.

EXAMPLES

The following Test Examples and Examples further illustrate the present invention in detail but are not to be construed to limit the scope thereof.

Here, the human recombinant HGF (hereinafter, referred to as hr-HGF) used in Test Examples was that which was purified from culture supernatant of CHO cells obtained by transfection of human recombinant HGF cDNA (Nakamura et al., Nature 342, 440–443, 1989; Seki et al., Biochem. Biophys. Res. Commun. 172, 321–327, 1990).

Test Example 1

Relieving action of HGF against side effect of cyclosporin was tested according to the following method.
1. Method The experimental design of this test is shown in FIG. 1. Acute organ disorder was prepared by daily intraperitoneal administration of 100 mg/kg of cyclosporin A (hereinafter, referred to as CsA) to ICR mice. hr-HGF (5 µg for individual per one dose) or a physiological saline as control (0.1 ml) was administered through a tail vein 30 minutes before the first CsA administration and then every 12 hours. In FIG. 1, times for doses of the above-mentioned medicines are indicated by black triangle marks (CsA) and white triangle marks (hr-HGF/physiological saline solution).

Further, mice were sacrificed 60 hours and 108 hours after the first CsA administration, and were subjected to blood examination, pathologic tissue examination and organ regeneration examination. In FIG. 1, times for sacrifices are indicated by star marks.
2. Results
(1) Survival rate The survival rate of test mice is shown in the lower graph of FIG. 1. In the control group, 83.3% of mice survived for 3 days and 50% of mice survived for 5 days. On the contrary, in the hr-HGF-treatment group, all mice survived. Between survival rates of these two groups, there was a significant difference with 5% significance level in logrank test.

In this way, it was found that administration of hr-HGF remarkably extended the survival of mice which had acute organ disorder caused by CsA.
(2) Phenomenon and Symptom Summary of phenomena and symptoms of the hr-HGF administered group and the control group are shown in Table 1. In the control group, middle to severe diarrhea was recognized in every example from 1 day after CsA administration. And, piloerection, hypokinesea and weakness condition were simultaneously recognized in most mice following temporary acrocinesia. After that, mice did not eat food, several mice died with intense convulsion.

On the other hand, in the hr-HGF-treated group, diarrhea was mild as compared with the control group. And, weakness condition, piloerection and convulsion were not recognized, and food eating was good and active condition was maintained.

With respect to body weight change, in the control group, the body weight was reduced to 93.6±9.6% of the initial body weight, whereas in the hr-HGF-treated group, the body weight increased to 102.5±3.0% of the initial body weight, and there was a significant difference with 5% significance level in unpaired Wilcoxon test.

In this way, it was found that administration of hr-HGF could ease the phenomena and symptoms of side effects by CsA.

TABLE 1

(phenomenon and symptom)

| Phenomenon and symptom | Control group | | hr-HGF administered group | |
|---|---|---|---|---|
| | 3 days after | 5 days after | 3 days after | 5 days after |
| Diarrhea | ++ | ++–+++ | + | + |
| Weakness condition | + | —+ | – | – |
| Piloerection | + | ++ | – | – |
| Convulsion | ++ | —+ | – | – |
| Amount of food to be eaten | Reduced | Not good | Good | Good |

In the table, –: Normal, +: Slight, ++: Middle, +++: Severe (3) Blood Examination In the control group, slight increases in GPT (Glutamate pyruvate transaminase) value and total bilirubin value were recognized, and mild hepatic disorder occurred. With respect to blood urea nitrogen value and creatinine value in blood, there was recognized no statistically significant difference between the values of the control group and those of hr-HGF-treated group.

(4) Histopathological Observation

As described above, with respect to the blood urea nitrogen value and creatinine value in blood, though there was recognized no statistically significant difference between the control group and hr-HGF-treated group, histological difference was recognized. In the control group, weak to middle level vacuolation in wide range in proximal tubules was recognized at 3 days after in every mouse, and such change was recognized also in three mice which survived to 5 days after.

On the other hand, in the hr-HGF-treated group, though weak vacuolation was recognized in 4 individuals from 5 individuals at 3 days after, and at 5 days after, kidney was in normal condition except that histologically slight topical renal tubular necrosis was recognized in two mice.

Here, middle to severe vacuolation and change in focal cells are shown in Table 2.

As shown in the above description and the result of Table 2, it was found that administration of hr-HGF could prevent the organ disorder caused by CsA.

TABLE 2

(histopathological observation of proximal tubules)

| Histological observation | Control group | | hr-HGF administered group | |
|---|---|---|---|---|
| | 3 days after | 5 days after | 3 days after | 5 days after |
| Vacuolation* | 2/6 | 2/3 | 2/5 | 0/5 |
| Change of focal cell* | 4/6 | 1/3 | 2/5 | 3/5 |

*number of animals which occurred middle–severe change/number of tested animals (5) Organ Regeneration Examination (DNA Synthesis)

To examine whether HGF promoted regenerations of kidney and liver or not, BrdU (5-bromo-2'-deoxyuridine) was injected into a mouse, subsequently the kidney and liver were stained by a BrdU specific immunocytochemical method, and DNA syntheses in the kidney and liver were measured. The results are shown in Table 3.

Ratio of the cells in DNA synthesis period (labeling index) in kidney was increased to 0.4% from 0.14% in the control group at 3 days after, and to 0.88% in the hr-HGF-treated group.

In liver, the labeling index in the control group was not more than 0.1% at 3 days after, and this value was approximately the same as that of a normal mouse. On the other hand, in the hr-HGF-treated group, it increased to 0.55%. There was a significant difference with 5% significance level in unpaired Wilcoxon test.

In this way, it was proved that, in the hr-HGF-treated group, increase of the labeling index was observed, DNA synthesis was actively conducted, and regenerations of kidney and liver were promoted.

Here, the measurement of the labeling index was conducted by a method of Ishiki et al. (Hepatology 16, 1227–1235, 1992).

TABLE 3

(DNA synthesis)

| | Labeling index at 3 days after | |
|---|---|---|
| DNA synthesis | Control group | hr-HGF administered group |
| Liver | 0.01 ± 0.01 *1 | 0.55 ± 0.42 *1 |
| Kidney | 0.40 ± 0.24 *2 | 0.88 ± 0.24 *2 |

*1: $p < 0.01$ in Wilcoxon test
*2: $p < 0.01$ in Wilcoxon test

Example 1

A solution containing 1 mg of HGF, 1 g of mannitol and 10 mg of polysorbate 80 in 100 ml of physiological saline was aseptically prepared. 1 ml of the solution was poured into each vial and lyophilized, and then the vial was sealed to obtain a freeze-dried preparation.

Example 2

A solution containing 1 mg of HGF and 100 mg of human serum albumin in 100 ml of 0.02M phosphate buffer (containing 0.15M of NaCl and 0.01% of polysorbate 80, pH 7.4) was aseptically prepared. 1 ml of the solution was poured into each vial and lyophilized, and then the vial was sealed to obtain a freeze-dried preparation.

Example 3

A solution containing 1 mg of HGF, 2 g of sorbitol, 2 g of glycine and 10 mg of polysorbate 80 in 100 ml of distilled water for injection was aseptically prepared. 1 ml of the solution was poured into each vial and lyophilized, and then the vial was sealed to obtain a freeze-dried preparation.

What is claimed is:

1. A method for relieving a side effect caused by immunosuppressants, which comprises:

administering an effective amount of hepatocyte growth factor (HGF) to reduce said side effect selected from the group consisting of hepatic disorder, kidney disorder, neuropathy, gastrointestinal disorder, anorexia, diarrhea, piloerection, fever and convulsion.

2. The method of claim 1, wherein the side effect is selected from the group consisting of nephrotoxicity, heptotoxicity, gastrointestinal disorder and neuropathy.

3. The method of claim 1, wherein the immunosuppressant is an antibiotic immunosuppressant.

4. The method of claim 1, wherein the immunosuppressant is an immunosuppressant which blocks intracellular signaling pathways which enhance expression of a lymphokine gene via activation of a T-cell antigen receptor (TCR) due to antigen stimulation in a T-cell.

5. The method of claim 1, wherein the immunosuppressant is an immunosuppressant which manifests effects by binding an immunophilin.

6. The method of claim 1, wherein the immunophilin is cyclophilin or FK506 binding protein.

* * * * *